(12) United States Patent
Mamiya et al.

(10) Patent No.: US 8,131,061 B2
(45) Date of Patent: Mar. 6, 2012

(54) APPARATUS FOR INSPECTING SOLDER PRINTING

(75) Inventors: Takahiro Mamiya, Aichi (JP); Tsuyoshi Ohyama, Aichi (JP)

(73) Assignee: CKD Corporation, Aichi (JP)

( * ) Notice: Subject to any disclaimer, the term of this patent is extended or adjusted under 35 U.S.C. 154(b) by 714 days.

(21) Appl. No.: 12/246,756

(22) Filed: Oct. 7, 2008

(65) Prior Publication Data

US 2009/0097738 A1 Apr. 16, 2009

(30) Foreign Application Priority Data

Oct. 10, 2007 (JP) ................................. 2007-264578

(51) Int. Cl.
*G06K 9/00* (2006.01)
(52) U.S. Cl. ..................................... 382/150; 356/237.1
(58) Field of Classification Search .................. 382/147, 382/150
See application file for complete search history.

(56) References Cited

U.S. PATENT DOCUMENTS 5,991,435 A * 11/1999 Tsujikawa et al. ............ 382/147
7,072,503 B2 * 7/2006 Prince ........................... 382/150

FOREIGN PATENT DOCUMENTS

JP 11-287627 A 10/1999
JP 2006-005238 A 1/2006

OTHER PUBLICATIONS

Notification of Reasons for Refusal for Japanese Application No. 2007-264578 mailed Oct. 20, 2009 and English translation thereof, 6 pages.

* cited by examiner

*Primary Examiner* — F. L. Evans
(74) *Attorney, Agent, or Firm* — Osha • Liang LLP

(57) ABSTRACT

An apparatus for inspecting solder printing includes a memory medium, an ideal solder information generation unit, and an image processing unit. Design data are stored in the memory medium. The ideal solder information generation unit generates "ideal solder position information" and "ideal solder sizes" from the ideal solder regions in the design data. The image processing means extracts the actual solder regions of solder on the printed board K from image data imaged by the CCD camera and generates "actual solder position information" from the actual solder regions. The image processing unit generates "position misalignment amounts" between the "ideal solder position information" and "actual solder position information," generates "print misalignment rates" indicating the extents of the "position misalignment amounts" relative to the "ideal solder sizes," calculates a correction value relating to print position based on the "print misalignment rates," and outputs a correction value signal to the solder printing machine.

20 Claims, 5 Drawing Sheets

APPARATUS FOR INSPECTING SOLDER PRINTING

TECHNICAL FIELD

The present invention relates to an apparatus for inspecting solder printing for inspection of solder printed on a board.

BACKGROUND ART

Generally when electronic components are mounted on a printed board, firstly a cream solder is printed on a certain electronic pattern disposed on the printed board. This printing of cream solder is carried out by screen printing by use of a silkscreen in which are formed multiple holes that correspond to the electrode pattern. The electronic components are provisionally held on the cream solder-printed board by viscosity of the cream solder. Thereafter, the printed board is carried to a reflow furnace, and soldering is performed as the printed board passes through a certain reflow process. In recent years, inspection of the condition of the solder printing has been performed during a stage prior to conveyance to the reflow furnace.

During this processing, there are concerns that manufacturing errors, shrinkage-stretching over time, and the like may occur for the silkscreen; and difficulties arise where perfect matching does not occur between the positions of the electrode pattern on the printed board and the positions of the holes formed in the silkscreen. For this reason, there is concern that the solder may be printed at positions displaced from the electrode pattern. Thus technology has been proposed (e.g., see Patent Citation 1) that finds a shift amount of the silkscreen that results in a minimum of the total of parallel movement displacement amounts of all solders printed on the board relative to the solder printing positions according to design (ideal printing positions), and performs correction of the printing positions based on this shift amount.

[Patent Citation 1] Unexamined Laid-open Patent Application 2006-5238.

However, when the above-mentioned technology is used, the shift amount is then determined uniformly without regard to the magnitude of the size of the solder. Thus when comparatively small solder is printed on a comparatively small electrode pattern, there is concern that this may result in printing at positions of relatively great displacement from the electrode pattern. As a result, problems occur such as non-printing of solder on the electrode pattern, printing that causes solder to connect together electrode patterns (bridging), and the like; and there are concerns that such problems would result in lowering of manufacturing quality and lowering of yield. Moreover, particularly for miniaturized electrode patterns, there have been further concerns that the frequency of occurrence of bridging and the like may then greatly increase and that manufacturing quality and yield may further decrease.

SUMMARY OF INVENTION

The present invention was accomplished in consideration of the above-mentioned circumstances. One or more embodiments of the present invention provide an apparatus for inspecting solder printing that is capable of improving manufacturing quality and yield while effectively suppressing solder printing failures.

The various means suitable for solving the above-mentioned problems will be explained below item-by-item. Furthermore, as may be required, the inherent operational effect for the corresponding means will be appended.

In one or more embodiments (1), an apparatus for inspecting solder printing includes an irradiation means capable of irradiating a light on solder printed on a board by a solder printing machine; an imaging means capable of imaging the solder irradiated by the light; an image processing means for extraction of an actual solder region, which is a solder region that has actually been printed, among a certain multiplicity of solders on the board based on image data imaged by the imaging means; and an ideal solder size generation means for generation of an ideal solder size indicating size the ideal solder regions and ideal solder position information indicating positions of the ideal solder regions on the board corresponding to the certain multiplicity of solders and based on the ideal solder regions which are solder regions in design data or manufacturing data; wherein the image processing means generates actual solder position information showing positions of actual solder regions on the board based on the actual solder regions; generates for each of the certain multiplicity of solders a print misalignment rate showing extent of positional misalignment between the ideal solder position information and the actual solder position information with respect to ideal solder size; and calculates a correction value based on the print misalignment rate, and outputs a correction value signal to the solder printing machine relating to solder printing position.

Moreover, the term "certain multiplicity of solders" means a multiplicity of solders selected by the operator and the like as targets for inspection, and this certain multiplicity of solders may be all of the solders provided on the board or may even be part of the solders. Moreover, the "actual solder position information" and the "ideal solder position information" indicate relative positions of solder regions relative to the board, and for example, these may indicate the center or center of mass of the solder region, the center or center of mass of a rectangle circumscribing the solder region, the range occupied by the solder relative to the board, and the like. In addition, the term "ideal solder size" means the size of solder under ideal printing conditions; and examples that can be cited are length of the ideal solder region in the X-axis direction or Y-axis direction, length of a diagonal line, surface area, volume, outline length, and the like. Also, examples that can be cited of the term "position misalignment amount" are distance along the X-axis or Y-axis between both solder position information (center or center of mass), linear distance between both solder position information, surface area of the actual solder region printed beyond the ideal solder position, and the like. Furthermore, examples that can be cited of the term "print misalignment rate" are absolute value of the value obtained by dividing the position misalignment amount by the ideal solder size, a value obtained by substitution of an absolute value of such in a certain function (e.g., membership function and the like), and the like.

According to the above-mentioned embodiments (1), the value for correction of printing position of the solder printing machine is calculated based on the "print misalignment rate" rather than being based simply on the "ideal solder position information," the "actual solder position information," and the "position misalignment amount." That is, a correction value (feedback) is determined based on a relative amount that is the extent of misalignment relative to the size of the printed solder (ideal solder size) rather than the absolute amount that is the "position misalignment amount." Because correction can be performed while considering size of the printed solder, it is possible to print each of the solders of each electrode pattern more accurately under conditions of relatively small extents of misalignment. Improvement of manufacturing quality and yield are possible, particularly for solders of comparatively small size, because printing which is highly misaligned from the electrode pattern can thus be effectively prevented.

Moreover, the solder printed after correction does not necessarily print at the anticipated positions, and there is concern that the resultant printing positions will have a certain degree of misalignment. However, according to the above embodiments, for the certain multiplicity of solders, corrections can be made to an extent such that misalignment of each solder relative to the electrode pattern would not be fatal. For this reason, is it possible to effectively suppress the occurrence of problems such as bridging and the like.

In one or more embodiments (2), the actual solder position information is information relating to coordinates showing relative position of the actual solder region with respect to the board; the ideal solder position information is information relating to coordinates showing relative position of the ideal solder region with respect to the board; the position misalignment amount is information of distance between both of these coordinates; and the ideal solder size is information of length of the ideal solder region corresponding to the information of distance between both of these coordinates.

Here, in the phrase "the ideal solder position information is information relating to coordinates showing relative position of the ideal solder region with respect to the board," for example, in the case of the above-mentioned distance information between both coordinates and when length is generated along the X-axis (Y-axis) between both coordinates, the term "ideal solder size" generates the length along the X-axis (Y-axis) of the ideal solder region corresponding to the above-mentioned X-axis (Y-axis).

According to the above-mentioned embodiments (2), the term "actual solder position information" is information relating to coordinates such as the central coordinates and the like of the actual solder region. The term "ideal solder position information" is information relating to coordinates such as the central coordinates and the like of the ideal solder region. Moreover, the term "position misalignment amount" indicates length information such as length between both coordinates in the X-axis direction or Y-axis direction, distance between both coordinates, and the like. Furthermore, "ideal solder size" generates length information of the ideal solder region corresponding to length information between both coordinates. That is, the "print misalignment rate" becomes specified from the standpoint of length information of the solder region, and the operational effect of above-mentioned embodiments (1) can be achieved with more certainty.

In one or more embodiments (3), the actual solder position information is information relating to a relative range of the actual solder region with respect to the board; the ideal solder position information is information relating to a relative range of the ideal solder region with respect to the board; the position misalignment amount, within the relative range of the actual solder region, is area of a part protruding from the relative range of the ideal solder region; and the ideal solder size is surface area of the ideal solder region.

According to the above-mentioned embodiments (3), the extent of the surface of the actual solder region printed beyond the ideal solder region becomes the "print misalignment rate." Therefore the "print misalignment rate" becomes determined while considering surface area of the solder region, and the operational effect of the above-mentioned means 1 can be achieved with more certainty.

In one or more embodiments (4), the image processing means updates, in order, the ideal solder position information by a certain update amount increment and finds the shift amounts; and each time that the position misalignment amounts are generated, generates the position misalignment amounts corresponding to the respective shift amounts, and also generates respective print misalignment rates for the certain multiplicity of solders.

The "certain update amount" is set arbitrarily according to the operator and the like based on electrode pattern layout on the board, shape of the board, and the like. Moreover, the "update" is updated, for example, by performance of updating by the certain update amount in the X-axis direction or the Y-axis direction, by updating in increments of the certain update amount (angle) of rotation around the center and the like of the printed board, and the like. In addition, the term "shift amount" means the total of updated amounts from a certain standard point. More particularly, if the certain standard point is "0," if the update in the X-axis direction is 3 increments of "0.1 mm," and if the update in the Y-axis direction is 2 increments of "0.1 mm," then the shift amount is the amount of movement, or the amount of movement required, for moving from the standard point by "0.3 mm in the X-axis direction" and "0.2 mm in the Y-axis direction."

According to the above-mentioned embodiments (4), the "ideal solder position information" is updated, in order, by increments of the certain update amount, and each "shift amount" is found. Also a "position misalignment amount" is generated corresponding to each "shift amount," and the "print misalignment rate" is generated from this "position misalignment amount." In other words, as the "ideal solder position information" is gradually updated (increments of the certain update amount), every update generates a "print misalignment rate"; and when this "print misalignment rate" is generated, a "shift amount" is found. That is, for example, if a certain calculation program is set up that is capable of so-called automatic "shift amount" determination, then the above-mentioned effect can be attained without much accompanying increased complexity of the details of control.

The term "special condition" means a condition that is capable of making the print misalignment rate of each solder comparatively small. Here, examples that can be cited of the "special condition," for example, are the aspects indicated by the below described embodiments (5) and embodiments (7).

In one or more embodiments (5), the apparatus finds a shift amount wherein a maximum print misalignment rate becomes minimum for the maximum print misalignment rate among the certain multiplicity of solder print misalignment rates corresponding to each of the shift amounts; and the apparatus determines the correction value based on this shift amount.

According to the above-mentioned embodiments (5), among the "print misalignment rates" of the certain multiplicity of solders corresponding to each "shift amount," the "maximum print misalignment rate" is found for the "shift amount" when the "maximum print misalignment rate" is smallest, and the above-mentioned correction value is determined based on this "shift amount." That is, among the certain multiplicity of solders, attention is paid to the solder that has the maximum "print misalignment rate" (greatest extent of misalignment), and correction is performed based on the "shift amount" when the extent of this misalignment of solder is smallest. That is, even for the solder that is most readily affected by misalignment, printing occurs within a range of comparatively small "print misalignment rate," and thus printing can be performed within ranges of even smaller "print misalignment rate" for other solders. As a result, manufacturing quality and yield can be further improved.

In one or more embodiments (6), for the maximum print misalignment rate among the print misalignment rates of the certain multiplicity of solders corresponding to the each of the shift amounts, when the minimum value among the maximum print misalignment rates is greater than or equal to a certain value, the board is determined to be defective; and a defect signal is output to the solder printing machine.

According to the above-mentioned embodiments (6), when the smallest value of the "maximum print misalignment rate" among the "print misalignment rates" of the certain multiplicity of solders is greater than or equal to a certain value, the board is determined to be defective, and a defect signal is output to the solder printing machine. That is, even through solder position correction has been performed, if the resultant solder print position remains greatly misaligned, then correction processing itself is not performed, and a defect signal is output to the solder printing machine. Thus, it is possible to effectively prevent manufacture of defective boards, and improvement of yield is possible.

In one or more embodiments (7), the apparatus determines the shift amount where solder print misalignment rates greater than or equal to a certain threshold value become less than or equal to a certain count; and the apparatus determines the correction value based on this shift amount.

According to the above-mentioned embodiments (7), the above-mentioned correction value is calculated based on a "shift amount" that is found when the "print misalignment rates" greater than or equal to the certain threshold value become less than or equal to a certain count for the "print misalignment rates" of the certain multiple of solders corresponding to each of the "shift amounts." That is, correction is performed such that the number of solders is relatively small which have comparatively large extents of print misalignment. Thus, solder is printed under conditions of an overall small degree of misalignment, and it is possible to greatly improve manufacturing quality and yield.

In one or more embodiments (8), updating of the ideal solder position information during finding of the shift amount is performed only within a certain range.

According to the above-mentioned embodiments (8), updating of the "ideal solder position information" is performed only within a certain range. For this reason, there is no determination of a useless shift amount due to updating at a useless range. As a result, processing can be performed more rapidly, and it is thus possible to improve manufacturing efficiency.

In one or more embodiments (9), the board is partitioned into a multiplicity of blocks; and the certain multiplicity of solders includes at least the solder of minimum size among solders in each block.

For comparatively small sized solder, printing can be greatly misaligned relative to the electrode pattern even though the position misalignment is comparatively small, and thus there is concern that all of the resultant boards may become defective due to such printing defects. For this reason, comparatively small sized solder requires printing relative to the electrode pattern that is much more accurate in comparison to relatively large sized solder. Concerning this issue, embodiments (9) partitions the board into multiple blocks, and the certain number of solders includes the solder of minimum size within each block. For this reason, it is possible to more accurately print solders of comparatively small size, and thus it is possible to suppress concerns that the all of the resultant boards may become defective due to it is possible to dramatically improve yield.

In one or more embodiments (10), the ideal solder information generation means generates a multiplicity of the ideal solder position information for a multiplicity of types of parameters; the image processing means generates a multiplicity of the actual solder position information according to the multiplicity of parameters; and the image processing means for the certain multiplicity of solders generates a multiplicity of the position misalignment amounts and the print misalignment rates for each of the parameters.

Here, the term "parameter" means various types of data indicating ideal (actual) solder position information. Examples are the center or center of mass and the like cited for the above-mentioned embodiments (1).

According to the above-mentioned embodiments (10), the "ideal solder position information" and the "actual solder position information" are generated for multiple types of parameters, and the correction signal is output to the solder printing machine based on the multiple "print misalignment rates" generated for the various parameters. That is, multi-faceted evaluation is possible based on the "print misalignment rates" of various types of parameters, and thus it is possible to more accurately understand the extent of misalignment of the solder. As a result, in comparison to the case of performance of correction based on the "print misalignment rate" generated for a single parameter, print position can be corrected more accurately, and it is possible to greatly improve manufacturing quality and yield.

DETAILED DESCRIPTION

Specific details of the present disclosure will now be described in detail with reference to the accompanying figures.

No. 1 Embodiment

Figure 1:
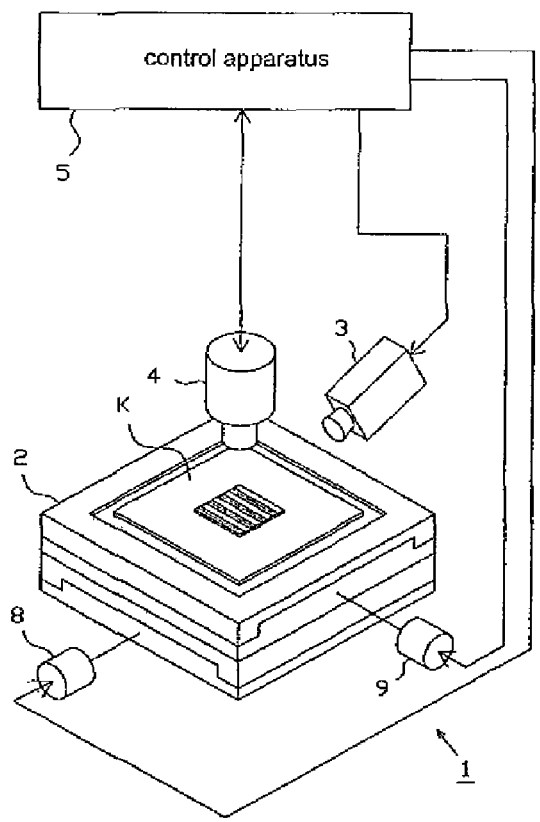
FIG. 1 shows a tilted perspective drawing of the apparatus for inspecting solder printing in accordance with one or more embodiments of the present invention.

FIG. 1 is a simplified structural drawing that shows schematically the apparatus for inspecting solder printing 1 of the present embodiment. As shown in this figure, the apparatus for inspecting solder printing 1 includes a stage 2 for carrying a printed board K, an irradiation means 3 for irradiation from an upwardly tilted direction of a certain light toward the surface of the printed board K, and a CCD camera 4 as an imaging means for imaging the region irradiated by the light on the printed board K. Moreover, the apparatus for inspecting solder printing 1 includes a control apparatus 5. This control apparatus 5 is constructed so as to perform control of the above-mentioned irradiation means 3, the CCD camera 4, and the like. This control apparatus 5 is also constructed for output of a certain feedback signal to a solder printing machine 15 (see FIG. 2) used for printing of cream solder on the printed board K.

Figure 3:
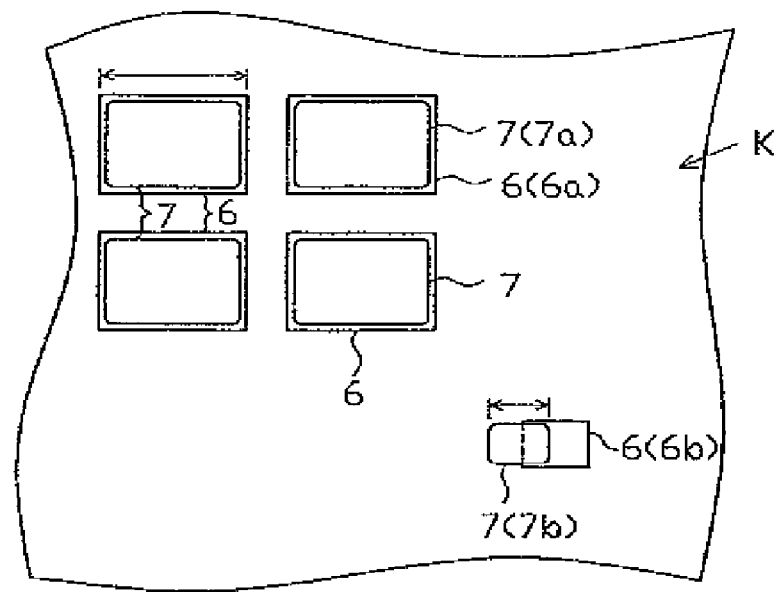
FIG. 3 shows a partial magnified top view of the printed board in accordance with one or more embodiments of the present invention.

Moreover, according to the present embodiment, the above-mentioned solder printing machine 15 prints (see FIG. 3; although FIG. 3 shows only part of the printed board K) cream solder (referred to hereinafter simply as "solder") of various different sizes on electrode patterns 6 of various different sizes on the printed board K. That is, the solder printing machine 15 includes a screen mask (not illustrated) in which are formed a multiplicity of holes at positions corresponding to the electrode pattern 6 on the printed board K, and this screen mask is used to make possible screen printing of the solder 7 on the printed board K. Moreover, multiple non-illustrated marks are provided on the printed board K, and based on these marks, positional alignment and the like of the printed board K is performed during solder printing 7. Based on the above-mentioned feedback signal, the solder printing machine 15 is able to adjust the relative positional relationship between the screen mask and the printed board K.

Returning to the explanation of the apparatus for inspecting solder printing 1 shown in FIG. 1, the above-mentioned stage 2 includes motors 8 and 9 which are disposed with mutually orthogonal rotation axes. Due to operation of these motors 8 and 9 by the above-mentioned control apparatus 5, the printed board K carried on the stage 2 can move by sliding in an arbitrary direction (X-axis direction and Y-axis direction). As a result, it becomes possible to cause movement of the visual field of the CCD camera.

The irradiation means 3 is capable of irradiation of a certain light toward the printed board K, and the COD camera 4 images the printed board K that is irradiated by light from the above-mentioned irradiation means. The image data imaged by this CCD camera 4 is send to a below described image processing means 13. In the present embodiment, brightness data is sent for light reflected from the printed board K as the image data. Moreover, rather than the brightness data, sending is also permissible of color data, height data, and the like of the printed board K.

Figure 2:
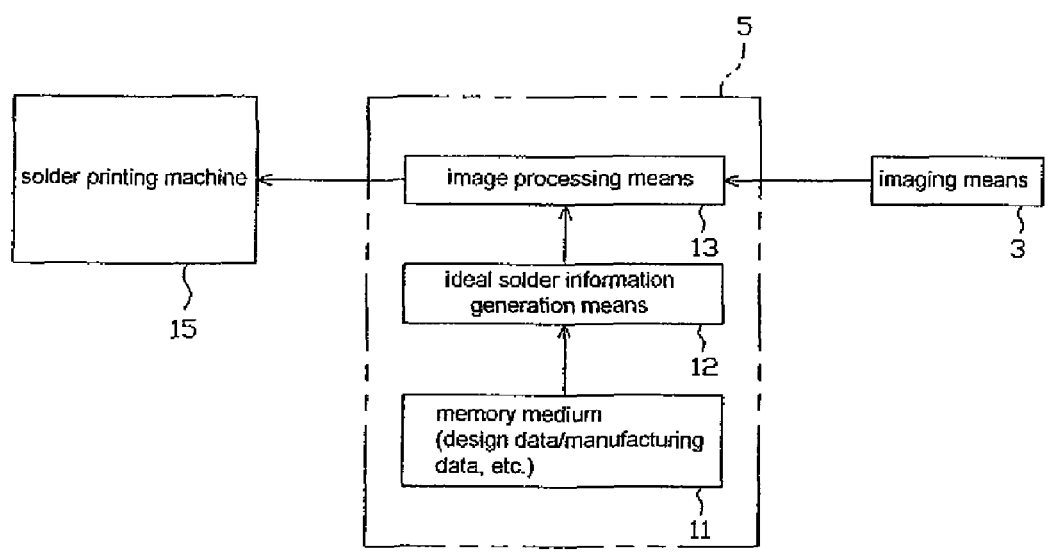
FIG. 2 shows a block diagram showing the control apparatus and the like in accordance with one or more embodiments of the present invention.

The control apparatus 5 will be explained next based on FIG. 2. The control apparatus 5 includes a memory medium 11, an ideal solder information generation means 12, and an image processing means 13.

Design data or manufacturing data for the printed board K are stored in the memory medium 11. In the present embodiment, the following are stored as design data or manufacturing data in this memory medium 11: positions or sizes of the electrode pattern 6 on the printed board K, size of solder 7 under ideal printing conditions (such as length of a side, surface area, outline length, diagonal length, volume, and the like of the solder 7), size of the printed board K, mark positions on the printed board K, and the like.

For a certain multiplicity of solders selected by the operator and the like, the ideal solder information generation means 12 generates "ideal solder position information" indicating various ideal solder regions and "ideal solder sizes" indicating sizes of the ideal solder regions from the ideal solder regions (which are solder regions for each solder in manufacturing data or in design data stored by the above-mentioned memory medium 11). Here the ideal solder information generation means 12 generates the "ideal solder position information" and the "ideal solder sizes" using previously set standard points and coordinate axes (X axis and Y axis indicating positions in a plane). Moreover, the ideal solder information generation means 12 is made capable of extracting the mark positions (called the "ideal mark positions") of the printed board K from within the design data or the manufacturing data. The "certain multiplicity of solders" may be all the solders on the printed board K or may be part of the solders.

In the present working example, the central coordinates (Lx, Ly) of the ideal solder region are generated as the "ideal solder position information." Moreover, it is also permissible to generate, for example, center of mass of the ideal solder region, center of mass or center of a rectangle circumscribing the ideal solder region, relative range of the ideal solder region with respect to the board, and the like as the "ideal solder position information."

In addition, in the present embodiment, the "ideal solder size" is generated as the length $(X_L)$ in the X-axis direction and as the length $(Y_L)$ in the Y-axis direction of the ideal solder region. Moreover, the "ideal solder size" may be generated as surface area, outline length, diagonal line length, and the like of the ideal solder region.

In addition, the ideal solder information generation means 12 sends to the above-mentioned image processing means 13 the generated "ideal solder position information," the "ideal solder sizes," and the "ideal mark positions."

Based on the above-mentioned image data imaged by the CCD camera 4, the image processing means 13 is able to extract from the solder regions those solder regions of the various solders 7 corresponding to the above-mentioned multiplicity of solders. In the present embodiment, the above-mentioned image data is subjected to binarization processing while using a certain brightness value as a threshold value, and thus it becomes possible to extract the actual solder regions. Moreover, the image processing means 13 is able to extract the mark positions (called the "actual mark positions") on the printed board K from within the above-mentioned imaging data.

Furthermore, based on the above-mentioned actual solder regions, the image processing means 13 generates "actual solder position information" that indicates the positions of these actual solder regions. Here, the image processing means 13 generates the "actual solder position information" using previously set standard points and coordinate axes (X axis and Y axis indicating position in a plane), and the central coordinates (x, y) of the actual solder regions are generated as the "actual solder position information" in the present embodiment. Moreover, it is also permissible to generate, for example, center of mass of the actual solder region, center of mass or center of a rectangle circumscribing the actual solder region, relative range of the real solder region with respect to the board, and the like as the "real solder position information."

Furthermore, by superimposing together of the above-mentioned "actual mark position" and the above-mentioned "ideal mark position," the image processing means 13 is able to align coordinates of the "actual solder position information" and the "ideal solder position information." By alignment of coordinates, although X-axis direction and Y-axis direction misalignments occur between the above-mentioned "ideal solder position information (Lx, Ly) and the "actual solder position information (x, y)," for convenient explanation hereinafter of the present embodiment, the post-alignment "ideal solder position information" will be expressed as (Lx, Ly), and the post-alignment "actual solder position information" will be expressed as (x, y).

Using the post-alignment coordinates, image processing means 13 calculates the "positional misalignment amounts" between the "actual solder position information" and the "ideal solder position information." In the present embodiment, a position misalignment amount "ΔX (=x−Lx)" along the X-axis direction and a position misalignment amount "ΔY (=y−Ly)" along the Y-axis direction between the "actual solder position information (x, y)" and the "ideal solder position information (Lx, Ly)" are generated as the above-mentioned "positional misalignment amounts." Alternatively, linear distance between both solder position information, surface area of the actual solder region printed protruding from the ideal solder position, and the like may be generated as the "position misalignment amount."

Furthermore, the image processing means 13 generates the "print misalignment rate" which is an absolute value of a number obtained by dividing the above-mentioned "position misalignment amount" by the above-mentioned "ideal solder size." In the present embodiment, an absolute value "|Δx/$X_L$|" number obtained by divided the "position misalignment amount Δx" by the "ideal solder size $X_L$" and an absolute value "|ΔY/$Y_L$|" number obtained by divided the "position misalignment amount Δy" by the "ideal solder size $Y_L$" and are calculated as the "print misalignment rates." That is, an "X-axis direction print misalignment rate" and a "Y-axis direction print misalignment rate," respectively, are generated.

Moreover, the image processing means 13 updates the "ideal solder position information" in certain update amount increments within a certain range, in order, and finds "shift amounts" for each update. Moreover, it is possible to generate (compute calculate) the "position misalignment amount" and "print misalignment rate," respectively, corresponding to each "shift amount." In other words, while the "ideal solder position information" is gradually updated (in increments of the certain update amount), each update "print misalignment rate" is generated; and the "shift amounts" are found when these "print misalignment rates" are generated. Here, the "ideal solder position information" is updated, in order, in the X-axis direction or Y-axis direction by increments of "0.2 mm" each within ranges of Lx≦Lx+5 mm and Ly−5 mm<Ly<Ly+5 mm; and the "shift amounts" are found for each update.

Updating of the "ideal solder position information" and the "shift amounts" will be explained specifically for the present embodiment. Firstly, updating is not performed in the X-axis direction, the "ideal solder position information" is updated in the above-mentioned update amount increments in the Y-axis direction, and the "shift amount" is found for each update. That is, the "ideal solder position information" is updated, in order, as (Lx, Ly−5), (Lx, Ly−4.8), (Lx, Ly−4.6), . . . (Lx, Ly+4.8), (Lx, Ly+5). Then "1 in the X-axis direction, −5 in the Y-axis direction," "0 in the X-axis direction, −4.8 in the Y-axis direction. "0 in the X-axis direction, −4.6 in the Y-axis direction," . . . "0 in the X-axis direction, +4.8 in the Y-axis direction," "0 in the X-axis direction, +5 in the Y-axis direction" are found as the "shift amounts." Next, Lx is updated by "+0.2 mm," and thus the "ideal solder position information" is updated in the above-mentioned update amount increments within the above-mentioned range in the Y-axis direction in the above-mentioned manner, and "shift amounts" are found for each update. That is, (Lx+0.2, Ly−5), (Lx+0.2, Ly−4.8), . . . (Lx+0.2, Ly+4.8), (Lx+0.2, Ly+5) are updated, in as the "ideal solder position information." Then "−0.2 in the X-axis direction, −5 in the Y-axis direction," "+0.2 in the X-axis direction, −4.8 in the Y-axis direction," . . . "+0.2 in the X-axis direction, +4.8 in the Y-axis direction," +0.2 in the X-axis direction, −5 in the Y-axis direction" are found as the "shift amounts." Thereafter, the "ideal solder information" is updated by updating Lx by "+0.2 mm" increments and in the above-mentioned update amount increments within the above-mentioned range in the Y-axis direction, and "shift amounts" are found for each update. Moreover, "position misalignment amounts" and "print misalignment rates" are generated corresponding to the various found "shift amounts."

If the position misalignment amount is "0" in the X-axis direction or the Y-axis direction for the respective certain multiplicity of solders that is the target of inspection, there is no revision of the "ideal solder position information" and there is no generation and the like of the "position misalignment amounts" and the "print misalignment rates." Accordingly, it is possible to omit calculating along a direction for which there is no position misalignment, and thus high speed processing can be performed.

In addition, the above-mentioned certain range and the above-mentioned "shift amount" can be set arbitrarily based on size of the printed board, layout of the electrode pattern 6, and the like.

Furthermore, the image processing means 13 finds the "shift amount" where the "maximum print misalignment rate" is minimum for the "maximum print misalignment rate" among the "print alignment rates" corresponding to the various "shift amounts." Here, although the "print alignment rate" has an "X-axis direction print misalignment rate" and a "Y-axis direction print misalignment rate," the respective "shift amount" is found that results in the smallest "maximum print misalignment rate" for the X-axis direction and the Y-axis direction, respectively. The shift amount "Bx" along the X-axis direction, the shift amount "By" along the Y-axis direction (as the "shift amounts"), and the initial "ideal solder position information" and the "ideal solder position information" when the above-mentioned "maximum print misalignment rate" becomes minimized are generated in the present embodiment.

Then the image processing means 13 calculates as the correction values "−Bx" and "−By" by sign inversion of the shift amounts "Bx" and "By," and the image processing means 13 outputs a feedback signal relating to these correction values to the above-mentioned solder printing machine 15. The solder printing machine 15 that receives the feedback signal relating to the correction values performs correction of the solder printing position by causing relative movement of the screen mask by "−Bx" in the X-axis direction and "−By" in the Y-axis direction with respect to the printed board K.

Next while referring to FIGS. 3, 4, 5, and 6, correction processing of the solder printing position by the apparatus for inspecting solder printing 1 of the above-mentioned configuration will be explained next using the flowchart of FIG. 7. For convenience during the explanation, correction processing of solder print position will be explained for the solders 7a and 7b printed on electrode patterns 6a and 6b, corresponding to the above-mentioned certain multiplicity of solders, among the solders 7 printed on the printed board K.

Firstly, the size of the solders 7a and 7b and the print condition of the solders 7a and 7b on the printed board K (target of inspection) will be explained (see FIG. 3).

Solder 7a is a solder of relatively large size, and for example, this has a X-axis direction width of "20 mm" and a Y-axis direction width of "10 mm." However, solder 7b is a solder of comparatively small size (e.g., X-axis direction width of "10 mm" and a Y-axis direction width of "5 mm," although these values are just hypothetical values). Moreover, although the solder 7a is printed accurately without misalignment in the X-axis direction and the Y-axis direction relative to the electrode pattern 6a, the solder 7b is printed with a "−5 mm" misalignment in the X-axis direction relative to the electrode pattern 6b. That is, the solder 7b is printed in a state of non-misalignment in the Y-axis direction. Solder 7a and solder 7b are printed at the ideal sizes.

Firstly during step S1, light is irradiated against this printed board K by the above-mentioned irradiation means 3. Then the above-mentioned CCD camera 4 images reflected light that is reflected from the printed board K and acquires image data.

Figure 4:
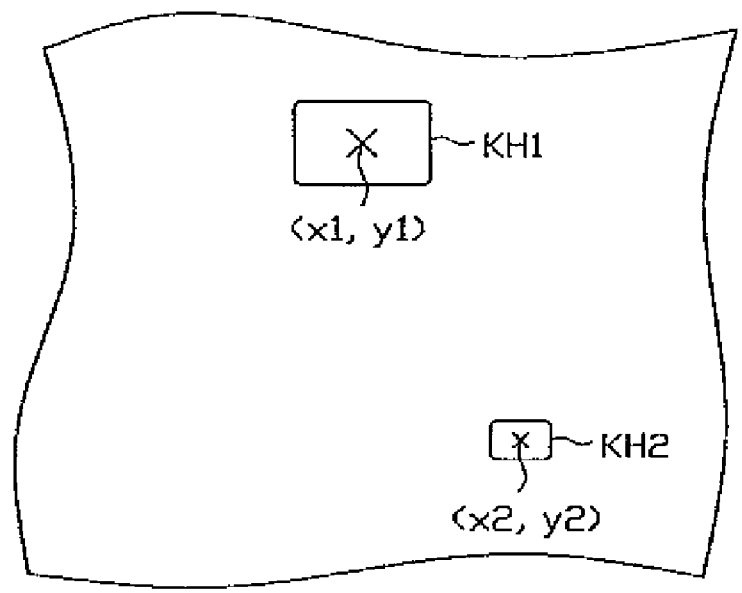
FIG. 4 shows a partial magnified schematic drawing showing the actual solder region and the like in accordance with one or more embodiments of the present invention.

Thereafter during step S2, the imaged image data is sent to the image processing means 13, and this image data is subjected to binarization processing. As shown in FIG. 4, the actual solder regions KH1 and KH2 are extracted for the solders 7a and 7b, respectively. Moreover, the "image mark positions" of the printed board K are also extracted from the image data.

Thereafter during step S3, the "actual solder position information" is generated for the solders 7a and 7b from the extracted actual solder regions KH1 and KH2. More specifically, the central coordinates (x1, y1) of the actual solder region KH1 are generated as the "actual solder position information" of the solder 7a, and the central coordinates (x2, y2) of the actual solder region KH2 are generated as the "actual solder position information" of the solder 7b.

Figure 5:
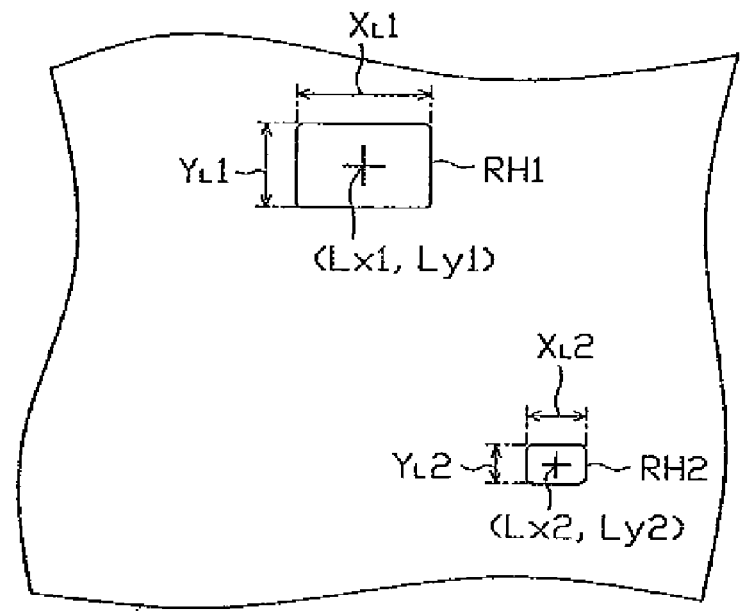
FIG. 5 shows a partial magnified schematic drawing showing the ideal solder region and the like in accordance with one or more embodiments of the present invention.

Then during step S4 as shown in FIG. 5, based on the ideal solder regions RH1 and RH2 from manufacturing data or from design data of the solders 7a and 7b, an "ideal solder position information" and an "ideal solder size" are each generated for solder 7a and 7b. That is, the central coordinates (Lx1, Ly1) of the ideal solder region RH1 are generated, and the length "$X_L1$" along the X-axis direction of the ideal solder region RH1 and the length "$Y_L1$" along the Y-axis direction of the ideal solder region RH1 are generated, as the "ideal solder position information" of the solder 7a. Also the central coordinates (Lx2, Ly2) of the ideal solder region RH2 are generated, and the length "$X_L2$" along the X-axis direction of the ideal solder region RH2 and the length "$Y_L2$" along the Y-axis direction of the ideal solder region RH2 are generated, as the "ideal solder position information" of the solder 7b. Moreover, specifically in the present embodiment, "$X_L1$" is generated as "20 mm," "$Y_L1$" is generated as "10 mm," "$X_L2$" is generated as "10 mm," and "$Y_L2$" is generated as "5 mm." Also the "ideal mark positions" are generated based on design data or manufacturing data.

The processing of this step S4 may be executed at an earlier step then the above-mentioned S1, and such processing may be executed between step S1 and step S2, or between step S2 and step S3. Moreover, the processing of step S4 may be executed in parallel with execution of the steps S1, S2, and S3.

Figure 6:
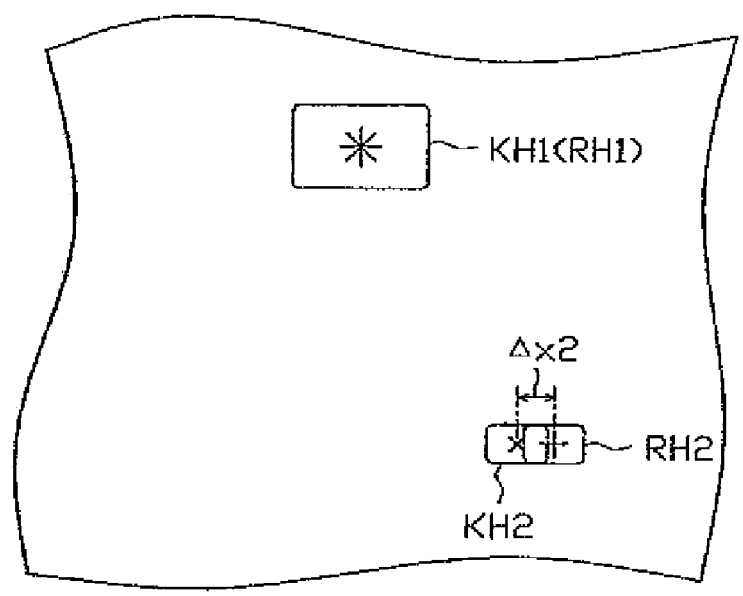
FIG. 6 shows a partial magnified schematic drawing showing alignment of coordinates of the actual solder position and the ideal solder position in accordance with one or more embodiments of the present invention.
Figure 7:
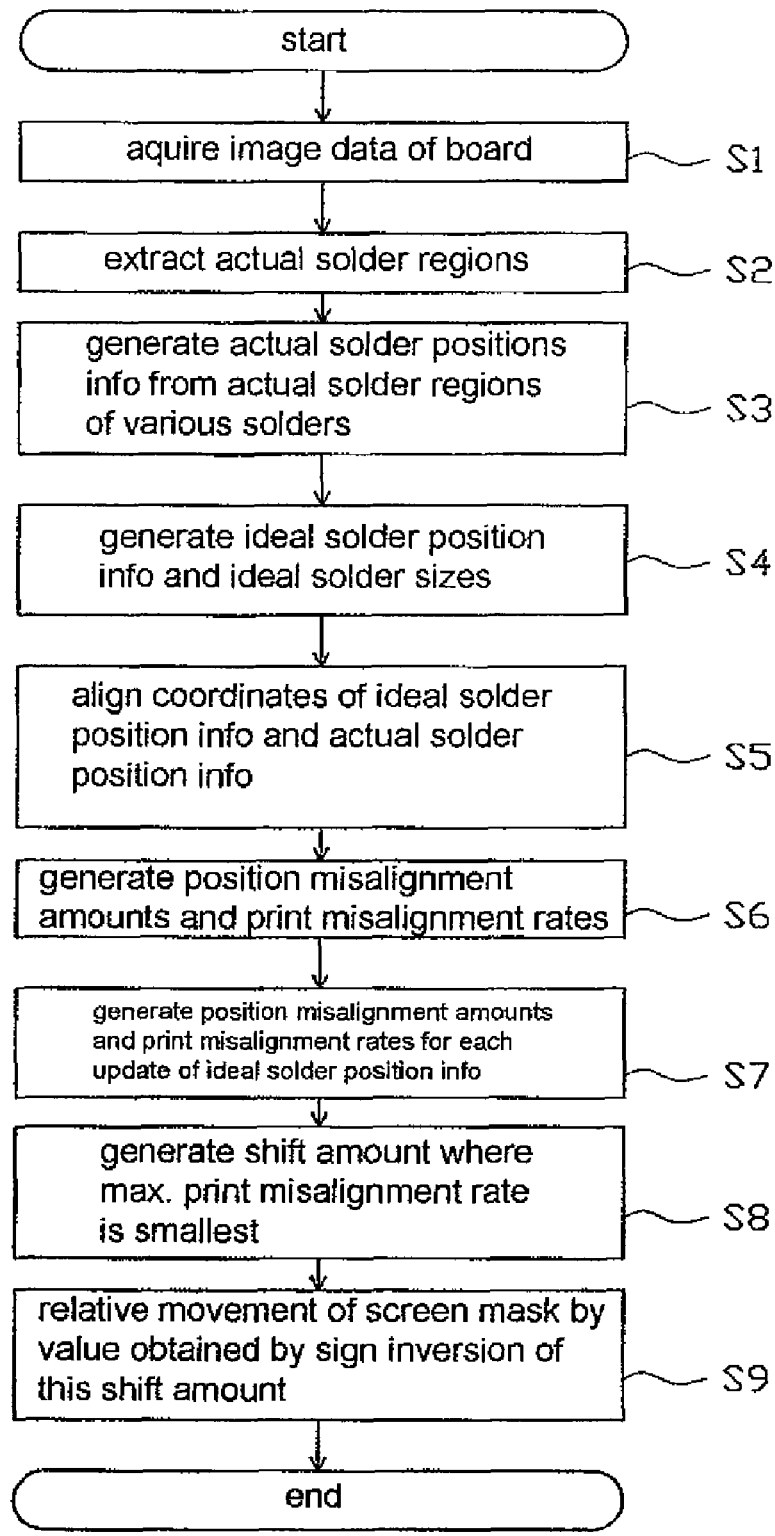
FIG. 7 shows a flowchart showing correction processing in accordance with one or more embodiments of the present invention.

Thereafter during step S5, the "actual mark positions" and the "ideal mark positions" are superimposed by the image processing means 13 as shown in FIG. 6, and alignment is performed of the coordinates of the "ideal solder position information" and the coordinates of the "actual solder position information" (e.g., revised as the post-alignment "actual solder position information").

Then during step S6, the "position misalignment amounts" are generated between the "ideal solder position information" and the "actual solder position information." In the present embodiment, since a position misalignment does not occur for the solder 7a as explained previously, the "actual solder position information (x1, y1)" and the "ideal solder position information (Lx1, Ly1)" match. Thus the "X-axis direction position misalignment amount $\Delta x1$" and the "Y-axis direction position misalignment amount $\Delta y1$" of the solder 7a are each generated as "0." However, since the printing for the solder 7b is misaligned by "−5 mm" in the X-axis direction as mentioned previously, an "X-axis direction position misalignment amount $\Delta x2$" of "−5 mm" and an "Y-axis direction position misalignment amount $\Delta y2$" of "0" of the solder 7b are generated.

Furthermore, by dividing the generated "position misalignment amounts" by the "ideal solder sizes," the absolute value of the resultant value generates the "print misalignment rate." In the present embodiment for the solder 7a, the "X-direction print misalignment rate ($|\Delta x1/X_L1|$)" and the "Y-direction print misalignment rate ($|\Delta y1/Y_L1|$)" each become "0." However, for the solder 7b, the "X-direction print misalignment rate ($|\Delta x2/X_L2|$)" becomes "0.5 (=|−5/10|)," and the "Y-direction print misalignment rate ($|\Delta y2/Y_L2|$)" becomes "0."

Thereafter during step S7, within the above-mentioned certain range, the "ideal solder position information" is updated, in order, by the certain update amount increments in the X-axis direction, and the "shift amounts" are found for each update. Also the "position misalignment amounts" and the "print misalignment rates" are generated corresponding to each "shift amount." In the present embodiment, since the "Y-axis direction position misalignment amount" for both solder 7a and solder 7b become "0," the update of the "ideal solder position information" and the "shift amount" calculation are not performed in the Y-axis direction, and there is no generation of the "position misalignment amounts" and the "print misalignment rates" corresponding to each "shift amount." In the present embodiment as shown in Table 1, a "position misalignment amount" and a "print misalignment rate" are each generated for the solders 7a and 7b along the X-axis direction corresponding to each "shift amount."

TABLE 1

| Shift amount | Position misalignment amount (mm) | | Print misalignment rate | | Maximum print misalignment rate |
|---|---|---|---|---|---|
| | Solder 7a | Solder 7b | Solder 7a | Solder 7b | |
| 0 | 0 | −5 | 0 | 0.5 | 0.5 |
| 0.2 | 0.2 | −4.8 | 0.01 | 0.48 | 0.48 |
| 0.4 | 0.4 | −4.6 | 0.02 | 0.46 | 0.46 |
| 0.6 | 0.6 | −4.4 | 0.03 | 0.44 | 0.44 |
| 0.8 | 0.8 | −4.2 | 0.04 | 0.42 | 0.42 |
| 1 | 1 | −4 | 0.05 | 0.4 | 0.4 |
| 1.2 | 1.2 | −3.8 | 0.06 | 0.38 | 0.38 |
| 1.4 | 1.4 | −3.6 | 0.07 | 0.36 | 0.36 |
| 0.6 | 0.6 | −3.4 | 0.03 | 0.34 | 0.34 |
| 0.8 | 0.8 | −3.2 | 0.04 | 0.32 | 0.32 |
| 2 | 2 | −3 | 0.1 | 0.3 | 0.3 |
| 2.2 | 2.2 | −2.8 | 0.11 | 0.28 | 0.28 |
| 2.4 | 2.4 | −2.6 | 0.12 | 0.26 | 0.26 |
| 2.6 | 2.6 | −2.4 | 0.13 | 0.24 | 0.24 |
| 2.8 | 2.8 | −2.2 | 0.14 | 0.22 | 0.22 |
| 3 | 3 | −2 | −0.15 | 0.2 | 0.2 |
| 3.2 | 3.2 | −1.8 | 0.16 | 0.18 | 0.18 |
| 3.4 | 3.4 | −1.6 | 0.17 | 0.16 | 0.17 |
| 3.6 | 3.6 | −1.4 | 0.18 | 0.14 | 0.18 |
| 3.8 | 3.8 | −1.2 | 0.19 | 0.12 | 0.19 |
| 4 | 4 | −1 | 0.2 | 0.1 | 0.2 |
| 4.2 | 4.2 | −0.8 | 0.21 | 0.08 | 0.21 |
| 4.4 | 4.4 | −0.6 | 0.22 | 0.06 | 0.22 |
| 4.6 | 4.6 | −0.4 | 0.23 | 0.04 | 0.23 |
| 4.8 | 4.8 | −0.2 | 0.24 | 0.02 | 0.24 |
| 5 | 5 | 0 | 0.25 | 0 | 0.25 |

Then during step S8, the "shift amount" is found that results in the smallest "maximum print misalignment rate" among the "maximum print misalignment rates" corresponding to each of the "shift amounts." In the present embodiment, when the "shift amount" is "+3.4 mm" in the X-axis direction, the "maximum print misalignment rate" among the "print misalignment rates" becomes "0.17," and this value becomes smaller than the "print misalignment rates" of the other various "shift amounts."

Then during step S9, these "shift amount" values are subjected to sign inversion to calculate the correction value as "−3.4 mm in the X-axis direction," and a feedback signal relating to this correction value is output to the solder printing machine 15. The solder printing machine 15 that has received the input feedback signal relating to correction, performs correction processing of the solder printing position by causing a relative shift of the screen mask of "−3.4 mm in the X-axis direction" with respect to the printed board K.

According to the apparatus for inspecting solder printing 1 of the present embodiment as explained previously in detail, the correction value relating to the printing position of the solder printing machine is calculated based on the "print misalignment rate" and not based simply on the "position misalignment amount" between the "ideal solder position information" and the "actual solder position information." That is, rather than based on the absolute amount which is the "position misalignment amount," the correction value is determined based of a relative amount which is the extent of misalignment relative to the printed solder size (ideal solder size). Accordingly, correction can be performed while considering the printed solder size, and thus it is possible to print under conditions of comparatively small degree of misalignment with accuracy for the various solders with respect to the various electrode patterns. It is possible to effectively prevent large misalignment of printing from the electrode pattern especially for solders of comparatively small size, and thus improvements of manufacturing quality and yield are possible.

Moreover, the solder printed after correction is not necessarily printed at the anticipated position, and there is concern that the solder may be printed at a position that is misaligned to a certain extent. However, according to the present embodiment, for the certain multiplicity of solders, correction is possible to an extent such that the various solder misalignments against the electrode patterns are not fatal. It is thus possible to effectively prevent the occurrence of problems such as bridging and the like.

Furthermore, the "shift amount" is found where this "maximum print misalignment rate" is smallest among the "print misalignment rates" of the certain multiplicity of solders corresponding to the various "shift amounts," and the above-mentioned correction value is determined based on this "shift amount." That is, among the certain multiplicity of solders, attention is paid to the solder that for which the "print misalignment rate" is largest (greatest extent of misalignment), and correction is performed based on the "shift amount" when the extent of this solder misalignment is smallest. That is, even for the solder that is most readily is affected by misalignment, printing becomes performed in a comparatively small range of "print misalignment rate," and thus it is possible to print within a range of "print misalignment rate" that is smaller than that of other solders. As a result, is it possible to further improve manufacturing quality and yield.

Also, the updating of the "ideal solder position information" is performed only within a certain range. Therefore, there is no finding of a useless "shift amount" due to updating within a useless range.

In addition, the above-mentioned "shift amount" can be set arbitrarily, and thus by setting the "shift amount" comparatively small, it is possible to perform correction of printing position with greater precision. On the other hand, by setting the "shift amount" to a relatively large value, it is possible to perform correction of the printing position relatively quickly. That is, it is possible to perform appropriate correction processing for various types of boards by the comparatively simple method of raising or decreasing the "shift amount."

No. 2 Embodiment

Next, figures will be referred to concerning the no. 2 embodiment which will be explained by concentrating on points of mutual difference with the above-mentioned no. 1 embodiment.

Figure 8:
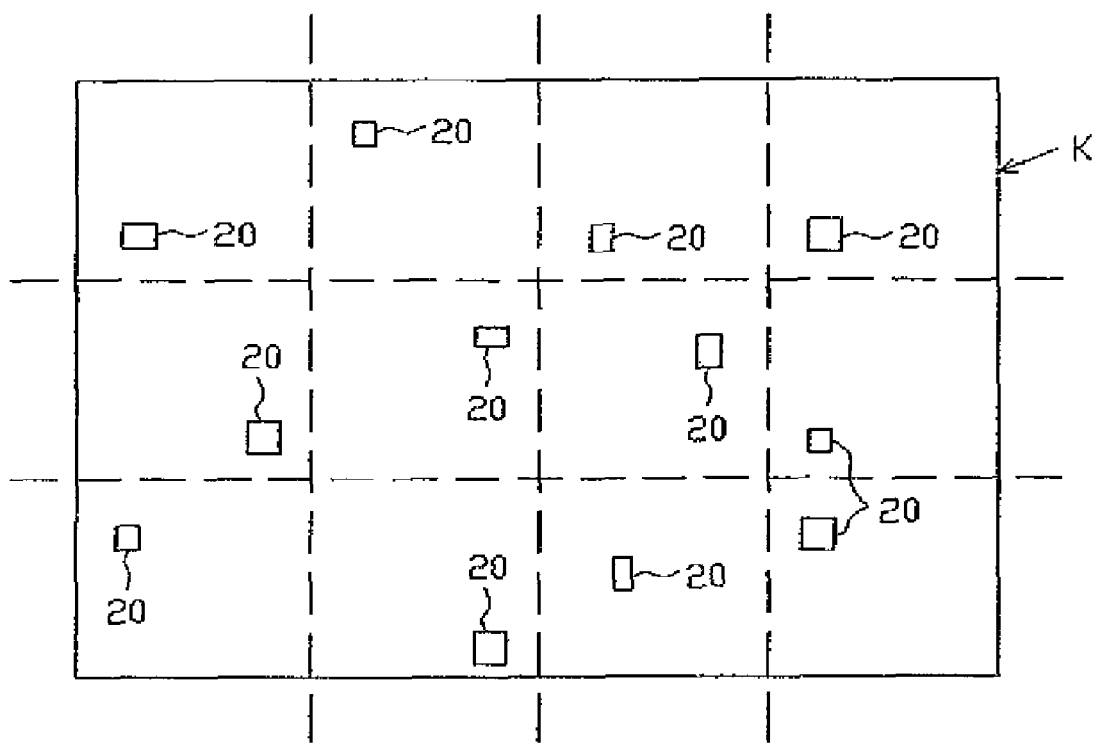
FIG. 8 shows a schematic top view for explanation of the certain multiplicity of solders of the printed board in accordance with one or more embodiments of the present invention.

According to the present embodiment, the above-mentioned certain multiplicity of solders that are the target of generation of the "actual solder position information," the "ideal solder position information," and the "ideal solder size" are set in the following manner. That is as shown in FIG. 8, the printed board K is partitioned into multiple blocks, the solder 20 of minimum size among the solders within each block is set as corresponding to the above-mentioned certain multiplicity of solders (although numerous solders are printed on the printed board K, only the solder 20 of minimum size among the various blocks is shown in FIG. 8). Then by performance of processing of the above-mentioned various steps with respect to the solder 20 set in this manner, calculation is performed of the correction amount relating to the printing position of the solder printing machine 15.

According to the above-mentioned present embodiment, the solder 20 of smallest size among the various blocks partitioned into a multiplicity of blocks of the printed board K is included in the certain multiplicity of solders. For this reason, it is possible to more accurately print the solder 20 of comparatively small size, it is thus possible to suppress concern that the entire printed board K may become defective, and thus it is possible to greatly improve yield.

Furthermore, these details of the above-mentioned embodiments are not limiting, and the present invention, for example, may be implemented in the following manners.

(a) Although according to the above-mentioned embodiment, the "print misalignment rate" was generated as "$|\Delta x/X_L|$" and "$|\Delta y/Y_L|$" the "print misalignment rate" is not limited to these values, and expression is permissible as an extent (ratio) of the "position misalignment amount" with respect to the "ideal solder size." For example, the "print misalignment rate" may be generated as: a value "$\{(\Delta x^2+\Delta y^2)/(X_L^2+Y_L^2)\}^n$" obtained by taking the nth power (2nd power and the like) of the value obtained by dividing distance between the central coordinates of both solder regions by diagonal length of the ideal solder region, a value "S/LS" obtained by dividing surface area "S" of the actual solder region protruding beyond the ideal solder region by the surface area "LS" of the ideal solder region, a value "$(\Delta x^2+\Delta y^2)/LS$" obtained by dividing the square of the distance between the central coordinates of both solder regions by the surface area "LS" of the ideal solder region, and the like. Moreover, a "print misalignment rate" may be used that is obtained by substituting such values into a certain formula (e.g., membership function and the like). Furthermore, two or more types of the "print misalignment rate" may be used. When two or more types of the "print misalignment rate" are used, much more accurate correction of the print position can be performed.

(b) According to the above-mentioned embodiment, a configuration was adopted that performed updating in increments of a certain update amount along the X-axis and Y-axis during updating of the "ideal solder position information." In contrast, adoption is also permissible of a configuration that updates the "ideal solder position information" by updating a center of rotation (central coordinate of the printed board K and the like) in increments of a certain value of degrees (e.g., 0.1°) within a certain range (e.g., −10° to +10°). It is also permissible to update "ideal solder position information" that combines various such configurations. By updating the "ideal solder position information" that combines various configurations, it is possible to perform correction of print position with great accuracy due to the possibility of generating a "shift amount" that is able to more greatly reduce the "print misalignment rate" among the certain multiplicity of solders.

(c) According to the above-mentioned embodiment, the "shift amount" was found where a "maximum print misalignment rate" became smallest for the "maximum print misalignment rates" among the certain multiplicity of solder "print misalignment rates" corresponding to each of the "shift amounts," and the correction value was calculated based on this "shift amount." However, calculation of the correction value is also permissible based on the "shift amount" when the 2nd largest or 3rd largest "print misalignment rate" among the "print misalignment rates" becomes smallest. Moreover, calculation of the correction value is also permissible based on a "shift amount" which is a value obtained by adding the "maximum print misalignment rate" and the "2nd largest print misalignment rate" becomes smallest.

(d) According to the above-mentioned embodiment, the "shift amount" was found where the "maximum print misalignment rate" among the "print misalignment rates" of the certain multiplicity of solders corresponding to the various "shift amounts" becomes smallest, and the correction value was calculated based on this "shift amount." In contrast, it is permissible to find a "shift amount" where the above-mentioned "print misalignment rate" greater than or equal to a certain threshold value becomes less than or equal to a certain number for the "print misalignment rates" of the certain multiplicity of solders corresponding to the various "shift amounts," and then to calculate the correction value of the print position based on this "shift amount." An example of this method will be explained in the case of generation of the respective values shown in Table 2 for the "position misalignment amount" and "print misalignment rate" corresponding to each "shift amount" for non-illustrated solders A, B, C, and D. Moreover, the adopted initial (pre-update ideal solder position information) "position misalignment amounts" are "0 mm" for solder A, "−5 mm" for solder B, "3 mm" for solder C, and "−10 mm" for solder D. Moreover, the "ideal solder size" is taken to be "20 mm" for solder A, "10 mm" for solder B, "20 mm" for solder C, and "40 mm" for solder D.

TABLE 2

| Shift amount (mm) | Position misalignment amount (mm) | | | | Position misalignment amount (mm) | | | | Threshold value (0.2) In conformance with condition? |
|---|---|---|---|---|---|---|---|---|---|
| | Solder A | Solder B | Solder C | Solder D | Solder A | Solder B | Solder C | Solder D | |
| 0 | 0 | −5 | 3 | −10 | 0 | 0.5 | 0.15 | 0.25 | X |
| 0.2 | 0.2 | −4.8 | 3.2 | −9.8 | 0.01 | 0.48 | 0.16 | 0.245 | X |
| 0.4 | 0.4 | −4.6 | 3.4 | −9.6 | 0.02 | 0.46 | 0.17 | 0.24 | X |
| 0.6 | 0.6 | −4.4 | 3.6 | −9.4 | 0.03 | 0.44 | 0.18 | 0.235 | X |
| 0.8 | 0.8 | −4.2 | 3.8 | −9.2 | 0.04 | 0.42 | 0.19 | 0.23 | X |
| 1 | 1 | −4 | 4 | −9 | 0.05 | 0.4 | 0.2 | 0.225 | X |
| 1.2 | 1.2 | −3.8 | 4.2 | −8.8 | 0.06 | 0.38 | 0.21 | 0.22 | X |
| 1.4 | 1.4 | −3.6 | 4.4 | −8.6 | 0.07 | 0.36 | 0.22 | 0.215 | X |
| 1.6 | 1.6 | −3.4 | 4.6 | −8.4 | 0.08 | 0.34 | 0.23 | 0.21 | X |
| 1.8 | 1.8 | −3.2 | 4.8 | −8.2 | 0.09 | 0.32 | 0.24 | 0.205 | X |
| 2 | 2 | −3 | 5 | −8 | 0.1 | 0.3 | 0.25 | 0.2 | X |
| 2.2 | 2.2 | −2.8 | 5.2 | −7.8 | 0.11 | 0.28 | 0.26 | 0.195 | X |
| 2.4 | 2.4 | −2.6 | 5.4 | −7.6 | 0.12 | 0.26 | 0.27 | 0.19 | X |
| 2.6 | 2.6 | −2.4 | 5.6 | −7.4 | 0.13 | 0.24 | 0.28 | 0.185 | X |
| 2.8 | 2.8 | −2.2 | 5.8 | −7.2 | 0.14 | 0.22 | 0.29 | 0.18 | X |
| 3 | 3 | −2 | 6 | −7 | 0.15 | 0.2 | 0.3 | 0.175 | X |
| 3.2 | 3.2 | −1.8 | 6.2 | −6.8 | 0.16 | 0.18 | 0.31 | 0.17 | ○ |
| 3.4 | 3.4 | −1.6 | 6.4 | −6.6 | 0.17 | 0.16 | 0.32 | 0.165 | ○ |
| 3.6 | 3.6 | −1.4 | 6.6 | −6.4 | 0.18 | 0.14 | 0.33 | 0.16 | ○ |
| 3.8 | 3.8 | −1.2 | 6.8 | −6.2 | 0.19 | 0.12 | 0.34 | 0.155 | ○ |
| 4 | 4 | −1 | 7 | −6 | 0.2 | 0.1 | 0.35 | 0.15 | X |
| 4.2 | 4.2 | −0.8 | 7.2 | −5.8 | 0.21 | 0.08 | 0.36 | 0.145 | X |
| 4.4 | 4.4 | −0.6 | 7.4 | −5.6 | 0.22 | 0.06 | 0.37 | 0.14 | X |
| 4.6 | 4.6 | −0.4 | 7.6 | −5.4 | 0.23 | 0.04 | 0.38 | 0.135 | X |
| 4.8 | 4.8 | −0.2 | 7.8 | −5.2 | 0.24 | 0.02 | 0.39 | 0.13 | X |
| 5 | 5 | 0 | 8 | −5 | 0.25 | 0 | 0.4 | 0.125 | X |

In this case, for example, the certain threshold value is set to "0.2," and the certain number is "1" (That is, the count of print misalignment rates that are greater than or equal to "0.2" is less than or equal to "1"). The "shift amounts" that match these conditions become "3.2 mm to 3.8 mm." For this reason, the "shift amount" is calculated as one of the values within this "3.2 mm to 3.8 mm." In this case, correction is performed such that the number of solders having a print misalignment of a comparatively large extent becomes relatively small. Accordingly, solder is printed under conditions of an overall small degree of misalignment, and it is possible to greatly increase manufacturing quality and yield.

(e) During finding of the "shift amount" that becomes the basis of the above-mentioned correction calculation, when the smallest value among the "maximum print misalignment rates" is greater than or equal to a certain number for the "maximum print misalignment rate" among the "print misalignment rates" of the above-mentioned certain multiplicity of solders corresponding to the various above-mentioned "shift values," the printed board K is determined to be defective, and a defect signal may be output to the solder printing machine 15. Accordingly, it is possible to prevent the resultant manufacture of defective boards, and thus yield can be greatly improved.

(f) According to the above-mentioned embodiment, only a single parameter was generated (center coordinates as the "actual solder position information" and the "ideal solder position information"). However, the "actual solder position information" and the "ideal solder position information" may be generated for multiple types of parameters. For example, in addition to the central coordinates, generation of the "actual solder position information" and the "ideal solder position information" is permissible as center of mass coordinates, relative range with respect to the solder region of the board, and the like. In this case, due to the ability to multilaterally evaluate the "print misalignment rate" for various types of parameters, it is possible to more accurately understand the extent of solder misalignment. As a result, in comparison to performance of correction based on a "print misalignment rate" generated from a single parameter, correction of print position can be performed more accurately, and it is possible to greatly improve manufacturing quality and yield.

(g) According to the above-mentioned embodiment, the "shift amount" was found where the "maximum print misalignment rate" becomes smallest in the X-axis direction and the Y-axis direction, respectively. In contrast, it is permissible to not distinguish between the "X-axis direction print misalignment rate" and the "Y-axis direction print misalignment rate," and to find a "shift amount" where the "maximum print misalignment rate" is smallest for the "maximum print misalignment rates" among these print misalignment rates.

| [Explanation of Item Numbering] | |
|---|---|
| 1 | apparatus for inspecting solder printing |
| 3 | irradiation means |
| 4 | CCD camera as the imaging means |
| 7, 7a, 7b, 20 | solder |
| 12 | ideal solder information generation means |
| 13 | image processing means |
| 15 | solder printing machine |
| K | printed board |
| KH1, KH2 | actual solder region |
| RH1, RH2 | ideal solder region |

What is claimed is:

1. An apparatus for inspecting solder printing comprising:
an irradiation unit operable to irradiate a light on solder printed on a board by a solder printing machine;
an imaging unit operable to image the solder irradiated by the light;
an image processing unit operable to extract an actual solder region, which is a solder region that has actually been printed, among a certain multiplicity of solders on the board based on image data imaged by the imaging unit; and
an ideal solder size generation unit operable to generate an ideal solder size indicating size the ideal solder regions and ideal solder position information indicating positions of the ideal solder regions on the board corresponding to the certain multiplicity of solders and based on the ideal solder regions which are solder regions in design data or manufacturing data;
wherein the image processing unit:
generates actual solder position information showing positions of actual solder regions on the board based on the actual solder regions;
generates for each of the certain multiplicity of solders a print misalignment rate showing extent of positional misalignment between the ideal solder position information and the actual solder position information with respect to ideal solder size; and
calculates a correction value based on the print misalignment rate, and outputs a correction value signal to the solder printing machine relating to solder printing position.

2. The apparatus for inspecting solder printing according to claim 1;
wherein the actual solder position information is information relating to coordinates showing relative position of the actual solder region with respect to the board;
the ideal solder position information is information relating to coordinates showing relative position of the ideal solder region with respect to the board; the position misalignment amount is information of distance between both of these coordinates; and
the ideal solder size is information of length of the ideal solder region corresponding to the information of distance between both of these coordinates.

3. The apparatus for inspecting solder printing according to claim 2;
wherein the actual solder position information is information relating to a relative range of the actual solder region with respect to the board;
the ideal solder position information is information relating to a relative range of the ideal solder region with respect to the board;
the position misalignment amount, within the relative range of the actual solder region, is area of a part protruding from the relative range of the ideal solder region; and the ideal solder size is surface area of the ideal solder region.

4. The apparatus for inspecting solder printing according to claim 1;
wherein the image processing unit: updates, in order, the ideal solder position information by a certain update amount increment and finds the shift amounts; and
each time that the position misalignment amounts are generated, generates the position misalignment amounts corresponding to the respective shift amounts, and also generates respective print misalignment rates for the certain multiplicity of solders.

5. The apparatus for inspecting solder printing according to claim 4;
wherein the image processing unit calculates a shift amount wherein a maximum print misalignment rate becomes minimum for the maximum print misalignment rate among the certain multiplicity of solder print misalignment rates corresponding to each of the shift amounts; and
wherein the image processing unit determines the correction value based on this shift amount.

6. The apparatus for inspecting solder printing according to claim 5;
wherein for the maximum print misalignment rate among the print misalignment rates of the certain multiplicity of solders corresponding to the each of the shift amounts, when the minimum value among the maximum print misalignment rates is greater than or equal to a certain value, the board is determined to be defective; and
a defect signal is output to the solder printing machine.

7. The apparatus for inspecting solder printing according to claim 4;
wherein the image processing unit determines the shift amount where solder print misalignment rates greater than or equal to a certain threshold value become less than or equal to a certain count; and
the apparatus determines the correction value based on this shift amount.

8. The apparatus for inspecting solder printing according to claim 4;
wherein updating of the ideal solder position information during finding of the shift amount is performed only within a certain range.

9. The apparatus for inspecting solder printing according to claim 1;
wherein the board is partitioned into a multiplicity of blocks; and the certain multiplicity of solders includes at least the solder of minimum size among solders in each block.

10. The apparatus for inspecting solder printing according to claim 1;
wherein the ideal solder information generation unit generates a multiplicity of the ideal solder position information for a multiplicity of types of parameters;
the image processing unit generates a multiplicity of the actual solder position information according to the multiplicity of parameters; and
the image processing unit for the certain multiplicity of solders generates a multiplicity of the position misalignment amounts and the print misalignment rates for each of the parameters.

11. An apparatus for inspecting solder printing comprising:
a camera operable to image solder printed on a board by a solder printing machine and irradiated by a light;
a control unit operable to extract an actual solder region, which is a solder region that has actually been printed, among a certain multiplicity of solders on the board based on image data imaged by the camera; and
an ideal solder size generation unit operable to generate an ideal solder size indicating size the ideal solder regions and ideal solder position information indicating positions of the ideal solder regions on the board corresponding to the certain multiplicity of solders and based on the ideal solder regions which are solder regions in design data or manufacturing data;
wherein the control unit;
generates actual solder position information showing positions of actual solder regions on the board based on the actual solder regions;
generates for each of the certain multiplicity of solders a print misalignment rate showing extent of positional misalignment between the ideal solder position information and the actual solder position information with respect to ideal solder size; and
calculates a correction value based on the print misalignment rate, and outputs a correction value signal to the solder printing machine relating to solder printing position.

12. The apparatus for inspecting solder printing according to claim 11;
wherein the actual solder position information is information relating to coordinates showing relative position of the actual solder region with respect to the board;
the ideal solder position information is information relating to coordinates showing relative position of the ideal solder region with respect to the board; the position misalignment amount is information of distance between both of these coordinates; and
the ideal solder size is information of length of the ideal solder region corresponding to the information of distance between both of these coordinates.

13. The apparatus for inspecting solder printing according to claim 12;
wherein the actual solder position information is information relating to a relative range of the actual solder region with respect to the board; the ideal solder position information is information relating to a relative range of the ideal solder region with respect to the board;
the position misalignment amount, within the relative range of the actual solder region, is area of a part protruding from the relative range of the ideal solder region; and
the ideal solder size is surface area of the ideal solder region.

14. The apparatus for inspecting solder printing according to claim 11;
wherein the control apparatus:
updates, in order, the ideal solder position information by a certain update amount increment and finds the shift amounts; and
each time that the position misalignment amounts are generated, generates the position misalignment amounts corresponding to the respective shift amounts, and also generates respective print misalignment rates for the certain multiplicity of solders.

15. The apparatus for inspecting solder printing according to claim 14;
wherein the control apparatus finds a shift amount wherein a maximum print misalignment rate becomes minimum for the maximum print misalignment rate among the certain multiplicity of solder print misalignment rates corresponding to each of the shift amounts; and
the control apparatus determines the correction value based on this shift amount.

16. The apparatus for inspecting solder printing according to claim 15;
wherein for the maximum print misalignment rate among the print misalignment rates of the certain multiplicity of solders corresponding to the each of the shift amounts, when the minimum value among the maximum print misalignment rates is greater than or equal to a certain value, the board is determined to be defective; and
a defect signal is output to the solder printing machine.

17. The apparatus for inspecting solder printing according to claim 14;
wherein the control apparatus determines the shift amount where solder print misalignment rates greater than or equal to a certain threshold value become less than or equal to a certain count; and
the control apparatus determines the correction value based on this shift amount.

18. The apparatus for inspecting solder printing according to claim 14;
wherein updating of the ideal solder position information during finding of the shift amount is performed only within a certain range.

19. The apparatus for inspecting solder printing according to claim 11;
wherein the board is partitioned into a multiplicity of blocks; and
the certain multiplicity of solders includes at least the solder of minimum size among solders in each block.

20. The apparatus for inspecting solder printing according to claim 11;

wherein the control apparatus generates a multiplicity of the ideal solder position information for a multiplicity of types of parameters; generates a multiplicity of the actual solder position information according to the multiplicity of parameters; and generates for the certain multiplicity of solders a multiplicity of the position misalignment amounts and the print misalignment rates for each of the parameters.

* * * * *